United States Patent [19]

Bentley et al.

[11] Patent Number: 4,696,763
[45] Date of Patent: Sep. 29, 1987

[54] COMPOSITIONS CONTAINING HETEROCYCLIC CORROSION INHIBITORS

[75] Inventors: Robert L. Bentley, Urmston; William Hoyle; James Jack, both of Stockport, all of England

[73] Assignee: CIBA-GEIGY Corporation, Ardsley, N.Y.

[21] Appl. No.: 730,028

[22] Filed: May 3, 1985

[30] Foreign Application Priority Data

May 11, 1984 [GB] United Kingdom ............... 8412063

[51] Int. Cl.$^4$ ........................................... C09K 15/30
[52] U.S. Cl. ................................. 252/391; 252/49.3; 252/49.5; 252/75; 252/78.1; 106/14.13; 106/14.14; 106/14.16; 106/14.24; 524/83; 548/165; 548/120; 548/171
[58] Field of Search ............ 252/391, 75, 78.1, 49.3, 252/49.5; 548/165, 170, 171; 524/83; 106/14.13, 14.14, 14.16, 14.24

[56] References Cited

U.S. PATENT DOCUMENTS

| | | | |
|---|---|---|---|
| 2,158,021 | 5/1939 | Lichty | 548/170 X |
| 2,222,354 | 11/1940 | Lichty | 548/170 X |
| 2,647,877 | 8/1953 | Dazzi | 548/170 X |
| 2,725,364 | 11/1955 | Dazzi | 524/83 |
| 2,772,277 | 11/1956 | D'Amico | 548/170 |
| 2,819,965 | 1/1958 | Murray et al. | 548/170 X |
| 2,861,918 | 11/1958 | Kosmin | 548/170 X |
| 2,939,789 | 6/1960 | Dersch et al. | 548/170 X |
| 3,049,509 | 8/1962 | Hardy et al. | 524/83 |
| 3,068,239 | 12/1962 | Miller | 548/170 |
| 3,379,875 | 4/1968 | Holoch | 524/83 |
| 3,657,318 | 4/1972 | Newallis et al. | 548/170 X |
| 4,000,079 | 12/1976 | Rasp et al. | 252/391 X |
| 4,011,194 | 3/1977 | Sandler | 548/170 X |
| 4,014,864 | 3/1977 | Kubba | 548/170 |
| 4,052,160 | 10/1977 | Cook et al. | 422/15 |
| 4,208,344 | 6/1980 | Dingwall et al. | 260/502.4 R |
| 4,235,838 | 11/1980 | Redmore et al. | 252/391 X |
| 4,265,769 | 5/1981 | Dingwall et al. | 210/699 |
| 4,329,381 | 5/1982 | Eschwex et al. | 252/391 X |
| 4,366,076 | 12/1982 | Clark | 252/34 |
| 4,376,000 | 3/1983 | Lindert | 148/6.15 R |
| 4,400,365 | 8/1983 | Haacke et al. | 423/306 |
| 4,612,049 | 9/1986 | Berner et al. | 106/14.13 |

FOREIGN PATENT DOCUMENTS

| | | | |
|---|---|---|---|
| 205022 | 12/1954 | Australia | 548/170 |
| 55248 | 6/1982 | European Pat. Off. | 548/170 |
| 67685 | 12/1982 | European Pat. Off. | |
| 126030 | 11/1984 | European Pat. Off. | 548/165 |
| 129506 | 12/1984 | European Pat. Off. | 548/165 |
| 128862 | 12/1984 | European Pat. Off. | |
| 2301461 | 7/1973 | Fed. Rep. of Germany | 524/83 |
| 3064 | 1/1979 | Japan | 548/170 |
| 73185 | 5/1982 | Japan | 252/392 |
| 204183 | 11/1983 | Japan | 548/170 |
| 564412 | 9/1944 | United Kingdom | |

OTHER PUBLICATIONS

Chem Abst. 90, 186930q (1979).
Chem Abst. 64, 3519e (1966).
Chem. Abst. 88, 201015z (1978).
S. Torii et al, Bull Chem Soc. Japan 52, 267 (1979).
Chem Abst. 97, 131683a (1982).
Edwards et al. "Nonmercurial Preservatives, Their Effectiveness and Relationship to Raw Materials in Latex Paint", J. Paint Technol., 46 (589) (Feb. 1974) pp. 37–45.

Primary Examiner—Matthew A. Thexton
Attorney, Agent, or Firm—Luther A. R. Hall

[57] ABSTRACT

New anticorrosive compositions comprise:
(A) an applicational medium selected from (a) surface coatings and (b) wholly or partly aqueous non-coating media,
(B) as corrosion inhibitor, an effective corrosion-inhibiting amount of at least one aliphatic or cycloaliphatic mono-, di-, tri- or tetra-carboxylic acid ester or anhydride which is substituted in the aliphatic or cycloaliphatic residue by one or more groups having the formula

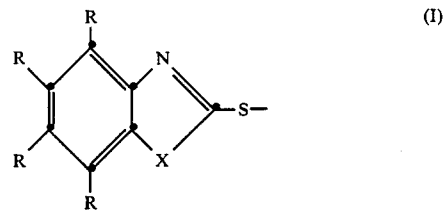

(I)

in which X is oxygen, sulphur or NH; and each R, independently, is hydrogen, alkyl, haloalkyl, alkoxy, alkylthio, alkylsulphonyl, cycloalkyl, phenyl, alkylphenyl, phenylalkyl, halogen, cyano, nitro, hydroxy, —COOH, —COOalkyl or a primary-, secondary- or tertiary amino- or carbamoyl group; or a non-toxic base addition salts of those components (B) which contain free carboxyl group.

24 Claims, No Drawings

COMPOSITIONS CONTAINING HETEROCYCLIC CORROSION INHIBITORS

The present invention relates to new compositions comprising as corrosion inhibitor, esters, partial esters or anhydrides of carboxylic acids which contain a heterocyclic residue; and to certain new compounds.

Effective corrosion inhibition is one of the most important requirements for organic coatings applied onto metal substrates. Many proposals for improving the corrosion inhibition of paints can be found in the literature e.g. in H. Kittel, Lehrbuch der Lacke und Beschichtungen, Band V, 1977. Thus the barrier function of the coatings may be improved thereby preventing corrosive agents such as oxygen, water and ions from reaching the metal surface where corrosion starts. Yet another possibility, most commonly practised today, is the addition of anticorrosive pigments which chemically, or electrochemically, interfere in the corrosion process by forming insoluble deposits with corrosion products e.g. alkali or metal ions, or by passivating (polarising) the metal surface. Amongst the most active anticorrosive pigments are metallic chromates and lead compounds (oxides etc.). Metallic chromates have been widely used as anticorrosive pigments in paints because of their activity in both the anodic and cathodic areas of protection. There is now some concern, however, about the environmental risks involved in the use of chromates because of their potential carcinogenic activity. Similarly, the chronic toxicity of lead compounds is causing great concern in the paint industry.

Metal salts of organic compounds have also proposed as corrosion inhibitors for use in coatings. In European Patent Specification No. 3817, for example, the use is described of zinc- or lead salts of hydroxyl- or mercapto compounds of 5- or 6-membered heterocyclic compounds which contain the characteristic group —N=C(OH)— or —N=C(SH)—. Typical examples are the zinc- and lead salts of 2-mercaptobenzothiazole. These known inhibitors, therefore, optionally also contain toxic lead salts.

In the surface coatings field, however, it has previously been doubted (Funke, Farbe und Lack, 87, 1981, 787) that the addition of organic corrosion inhibitors alone could provide sufficient corrosion inhibition in practice.

We have now found certain heterocyclic carboxylic acid esters and anhydrides, and their non-toxic salts, which are useful as corrosion inhibitors in surface coatings and which allow the formulation of highly effective chromate- and lead-free anticorrosive paints. The new corrosion inhibitors are not pigments and their use in surface coatings thus leaves the formulator a free choice of pigment or filler.

It is therefore surprising that the organic ester and anhydride corrosion inhibitors used according to the invention exhibit in surface coatings a corrosion-inhibiting effect which is comparable to, or even better than that of toxic chromate- or lead pigments. Moreover, these organic corrosion inhibitors exhibit excellent corrosion inhibition in wholly or partly aqueous non-coating media.

The present invention provides a composition comprising:

(A) an applicational medium selected from (a) surface coatings and (b) wholly or partly aqueous non-coating media; and (B) as corrosion inhibitor, an effective corrosion-inhibiting amount of at least one aliphatic- or cycloaliphatic mono-, di-, tri- or tetra-carboxylic acid ester or anhydride which is substituted in the aliphatic- or cycloaliphatic residue by one of more groups, preferably only one group, having the formula I

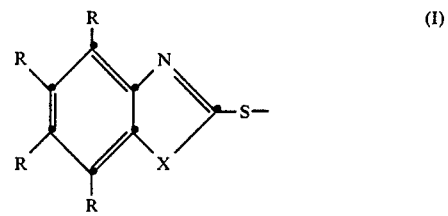

in which X is oxygen, sulphur or NH; and each R, independently, is hydrogen, alkyl, haloalkyl, alkoxy, alkylthio, alkylsulphonyl, cycloalkyl, phenyl, alkylphenyl, phenylalkyl, halogen, cyano, nitro, hydroxy, —COOH, —COOalkyl or a primary-, secondary- or tertiary amino- or carbamoyl group; or a non-toxic base addition salt of those components (B) which contain free carboxyl groups.

By "esters" of aliphatic or cycloaliphatic mono-, di-, tri- or tetra-carboxylic acids, we mean their full or partial esters containing 1 to 4 —COOH or —COOZ groups in which Z is $C_1$–$C_{18}$ alkyl optionally interrupted by one or more O or S atoms or by one or more $NR^o$ groups (wherein $R^o$ is $C_1$–$C_{18}$ alkyl, $C_5$–$C_8$ cycloalkyl, phenyl, naphthyl, $C_7$–$C_9$ phenylalkyl or $C_7$–$C_{18}$ alkylphenyl) or optionally substituted by e.g. SH, $COOR^o$ (wherein $R^o$ has its previous significance) $CONH_2$, CN or halogen (preferably F, Cl or Br); $C_2$–$C_{10}$ hydroxyalkyl optionally interrupted by one or more $NR^o$ groups (wherein $R^o$ has its previous significance) or O atoms; $C_2$–$C_{18}$ alkenyl; $C_3$–$C_{12}$ cycloalkyl, optionally substituted by e.g. $C_1$–$C_4$ alkyl, OH, SH, $COOR^o$, (wherein $R^o$ has its previous significance) $CONH_2$, CN or halogen (preferably F, Cl or Br); $C_7$–$C_9$ phenylalkyl, $C_7$–$C_{18}$ alkylphenyl; or $C_6$–$C_{10}$ aryl in which the phenyl or aryl residues, respectively, may be substituted e.g. by $C_1$–$C_{12}$ alkoxy, $C_1$ $C_{14}$ alkylthio, COOH, OH, halogen (preferably F, Cl or Br) or nitro; provided that at least one group —COOZ is present. In aliphatic- or cycloaliphatic compounds containing more than one group —COOZ, the individual groups Z may be the same or different.

By "anhydrides" of aliphatic or cycloaliphatic monocarbocyclic acids, we mean symmetrical or non-symmetrical anhydrides.

By "anhydrides" of aliphatic or cycloaliphatic di-, tri- or tetra-carboxylic acids we mean cyclic anhydrides containing the grouping III or IIIa

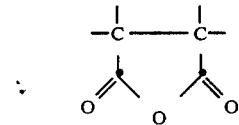

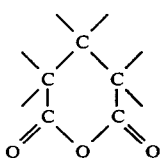
(IIIa)

Depending on whether X is oxygen, sulphur or NH, the esters and anhydrides used in the compositions of the invention are benzoxazoles, benzthiazoles or benzimidazoles; benzthiazoles are preferred.

R as alkyl, alkoxy, alkylthio or alkylsulphonyl, preferably contains 1–12 C-atoms, especially 1–6 C-atoms. Examples include methyl, ethyl, n-propyl, isopropyl, n-butyl, isobutyl, tert.-butyl, n-pentyl, n-hexyl, n-octyl, 1:1:3:3-tetramethylbutyl, n-nonyl, n-decyl, n-undecyl, n-dodecyl and t-dodecyl, and the corresponding alkoxy-, alkylthio- and alkylsulphonyl radicals.

R as cycloalkyl preferably contains 3–12 C-atoms preferably 5–8 C-atoms e.g. cyclopropyl, cyclobutyl, cyclopentyl, cyclohexyl, cyclooctyl or cyclododecyl.

R as haloalkyl preferably contains 1–4 C-atoms and 1–3 F- or Cl-atoms e.g. chloromethyl, fluoromethyl, di- and trifluormethyl or 2-chloroethyl.

R as alkylphenyl preferably contains 7–18 C-atoms and is e.g. tolyl, xylyl, 4-isopropylphenyl, 4-tert.-butylphenyl, 4-octylphenyl or 4-dodecylphenyl.

R as phenylalkyl preferably contains 7–9 C-atoms and is e.g. benzyl, 1-phenylethyl, 2-phenylethyl, α,α-dimethylbenzyl or 3-phenylpropyl.

R as halogen is preferably fluorine, chlorine or bromine.

When R is —COO alkyl, the alkyl group preferably has 1 to 4 C-atoms.

R as amino group or carbamoyl group preferably has up to 20 C-atoms. Examples are —$NH_2$, —$NHCH_3$, —$NHC_2H_5$, —$NHCH_2CH_2OH$, —$NHC_{20}H_{41}$, —NH-cyclohexyl, —NH-phenyl, —$N(CH_3)_2$, —$N(n-C_4C_9)_2$, —$N(CH_2CH_2OH)_2$, —$N(CH_3)(benzyl)$, morpholino, piperidino, —$CONH_2$, —CONH-phenyl, —$CONHC_8H_{17}$, —$CON(C_2H_5)_2$, —$CON(CH_2$-$H_2OH)_2$, morpholinocarbonyl or piperidinocarbonyl.

It is preferred that one of the substituents R is hydrogen, $C_1$–$C_4$ alkyl or $C_1$–$C_4$ alkoxy and that the other three groups R are each hydrogen. It is particularly preferred that all four groups R are each hydrogen.

When the group Z is a $C_1$–$C_{18}$ straight or branched chain alkyl group it may be, for example, a methyl, ethyl, n-propyl, iso-propyl, n-butyl, s-butyl, t-butyl, n-pentyl, n-hexyl, n-heptyl, n-octyl, 2-ethyl-hexyl, t-octyl, n-nonyl, n-decyl, n-dodecyl, n-tetradecyl, n-hexadecyl or n-octadecyl group.

When the group Z is a $C_1$–$C_{18}$ alkyl group optionally interrupted by one or more O, S or $NR^o$ it may be, for example, 2-methoxy-ethyl, 3-methoxy-propyl, 2-ethoxy-ethyl, 2-ethoxy-propyl, 3-ethoxy-propyl, 2-n-butoxy-ethyl, 2-(2-ethoxy-ethoxy)-ethyl, or 2-n-hexadecyloxyethyl, 2-dimethylamino-propyl, 2-dibutylamino-ethyl, 2-(methylphenylamino)-ethyl, 2-butylthioethyl or 2-tert.-dodecylthioethyl.

When Z is alkyl substituted by SH, —$COOR^o$, —$CONH_2$, —CN or halogen, it may be e.g. 2-mercaptopropyl, 3-mercaptopropyl, ethoxycarbonylmethyl, 2-isopropoxycarbonylethyl, 2-carbamoylethyl, 2-cyanoethyl, 2-chloroethyl or 3-chloropropyl.

When the group Z is a $C_2$–$C_{10}$ hydroxyalkyl group optionally interrupted by one or more $NR^o$ groups (wherein $R^o$ has its previous significance) or O atoms it may be e.g. a hydroxyethyl, hydroxypropyl, hydroxybutyl, hydroxydecyl, hydroxyethoxyethyl or N-hydroxyethyl-2-methylaminoethyl group.

When the group Z is a $C_2$–$C_{18}$ straight or branched chain alkenyl group it may be, for example, a vinyl, n-propenyl, iso-propenyl, n-butenyl, i-butenyl, n-pentenyl, n-hexenyl, n-hexadienyl, n-heptenyl, n-octenyl, n-nonenyl, n-decenyl, n-dodecenyl, n-tetradecenyl, n-hexadecenyl or n-octadecenyl group.

When the group Z is a $C_3$–$C_{12}$ preferably $C_5$–$C_8$ optionally substituted cycloalkyl group it may be e.g. cyclopropyl, cyclobutyl, cyclopentyl, cyclohexyl, cyclooctyl, cyclodecyl, cyclododecyl, 4-hydroxycyclohexyl, 4-mercaptocyclooctyl or 4-chlorocyclohexyl.

When the group Z is a $C_7$–$C_9$ phenylalkyl group it may be, for example, benzyl, 1-phenylethyl, 2-phenylethyl, α,α-dimethylbenzyl or 3-phenylpropyl.

When the group Z is a $C_7$–$C_{18}$ alkylphenyl group it may be, for example, tolyl, xylyl, 4-isopropylphenyl, 4-t-butylphenyl, 4-octylphenyl or 4-dodecylphenyl.

When the group Z is unsubstituted or substituted $C_6$–$C_{10}$ aryl, it may be e.g. phenyl, 3-chlorophenyl, 2,4-dichlorophenyl, 4-nitrophenyl, 3-hydroxyphenyl, 4-methoxyphenyl, 3-isopropoxyphenyl, 4-(methylthio)-phenyl, 2-carboxyphenyl, 1-naphthyl, 2-naphthyl or 4-chloro-1-naphthyl.

Preferably the group Z is $C_1$–$C_{18}$ alkyl optionally interrupted by O or substituted by —OH, —SH or halogen or Z is allyl, cyclohexyl, benzyl, phenyl, tolyl or naphthyl.

Component (B) of the compositions of the invention is preferably a saturated or unsaturated aliphatic- or cycloaliphatic mono-, di, tri- or tetra-carboxylic acid ester (as hereinbefore defined) or anhydride (as hereinbefore defined) substituted by one group of formula I.

Preferred components (B) are a compound of formula II

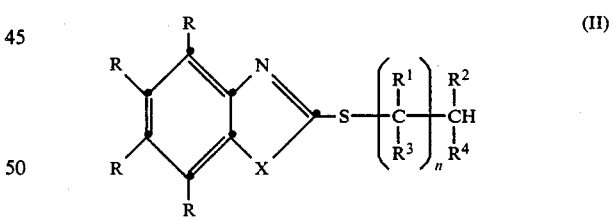

(II)

in which X and R have their previous significance; n is 0 or 1; and $R^1$, $R^2$, $R^3$ and $R^4$, independently, are hydrogen, alkyl, hydroxyalkyl, haloalkyl, alkoxyalkyl, optionally mono- or di-substituted phenyl or phenylalkyl, —COOH, —COOZ or alkyl substituted by 1, 2 or 3 —COOH or —COOZ, wherein Z has its previous significance, or (B) is a compound of formula II, wherein two groups —COOH present in the residue [—$(C(R^1)(R^3))$—$_n CH(R^2)(R^4)$] are cyclised to form an anhydride group of formula III or IIIa, or $R^1$ and $R^2$, or $R^1$ and $R^3$, together form an optionally branched alkylene group optionally substituted by one or two groups —COOZ or —COOH or $R^1$ and $R^2$ together constitute a direct bond; whereby in any case the residue

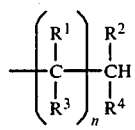

contains at least one group selected from —COOZ, formula III or formula IIIa.

Compound (B) may also be a non-toxic base addition salt of a compound of formula II which contains a free carboxyl group.

The anhydride group III or IIIa may be formed by cyclisation of (a) two —COOH groups $R^1$, $R_2$, $R^3$ or $R^4$; (b) two —COOH groups present when $R^1$, $R^2$, $R^3$ or $R^4$ is alkyl substituted by —COOH; or (c) two —COOH groups present when $R^1$ and $R^2$ or $R^1$ and $R^3$ are branched chain alkylene groups substituted by two —COOH groups.

$R^1$, $R^2$, $R^3$ and $R^4$ as alkyl are preferably $C_1$–$C_{18}$ alkyl e.g. methyl, ethyl, n-propyl, isopropyl, n-butyl, isobutyl, tert.-butyl, n-pentyl, n-hexyl, n-octyl, n-dodecyl, or n-octadecyl. As hydroxyalkyl or halogenalkyl, these substituents preferably have 1–4 C-atoms e.g. hydroxymethyl, 1- or 2-hydroxyethyl, 2- or 3-hydroxypropyl, chloromethyl, bromoethyl or bromoisopropyl. As alkoxyalkyl, these substituents preferably have 2–10 C-atoms e.g. methoxymethyl, 1-methoxyethyl, 2-ethoxypropyl, 2-methoxyethyl, 2ethoxypropyl, 1-methoxybutyl, n-butoxymethyl or 4-isopropoxybutyl.

When $R^1$, $R^2$, $R^3$ and $R^4$ is alkyl substituted by —COOH or —COOZ, the alkyl residue has preferably 2–12 C-atoms. Examples for such residue are —CH$_2$COOCH$_3$, —CH$_2$CH$_2$COOH, —CH(CH$_3$)COOC$_2$H$_5$, —CH$_2$CH$_2$CH$_2$COOC$_2$H$_5$, —CH$_2$CH(COOH)CH$_2$COOC$_4$H$_9$, —(CH$_2$)$_5$CH$_2$COOC$_3$H$_7$-iso, —CH(COOH)CH$_2$COOCH$_3$, or —CH$_2$CH(COOC$_2$H$_5$)CH(COOC$_2$H$_5$)CH$_2$COOC$_2$H$_5$.

When $R^1$, $R^2$, $R^3$ and $R^4$ are phenyl or phenylalkyl groups, the respective phenyl moieties in the groups may be mono- or di-substituted by halogen, $C_1$–$C_4$ alkyl, $C_1$–$C_4$ alkoxy, carboxy or hydroxy, examples being 4-chlorophenyl, tolyl, xylyl, 3-methoxyphenyl, 4-isopropylphenyl, 3-carboxyphenyl, 4-hydroxyphenyl, 4-bromobenzyl, 4-tert.-butylbenzyl, 2-phenylethyl or 3-phenylpropyl, but preferably phenyl or benzyl.

When $R^1$ and $R^2$, or $R^1$ and $R^3$ together are alkylene, then they form, together with the C-atoms to which they are bonded, a cycloalkane ring, preferably a cyclopentane or cyclohexane ring which may be substituted by alkyl groups, especially $C_1$–$C_4$ alkyl groups, or by one or two groups —COOH or —COOZ.

When $R^1$ and $R^2$ together denote a direct bond, the compounds of formula II are unsaturated carboxylic acid esters or anhydrides.

Base addition non-toxic salts are metal-, ammonium- and organic ammonium salts, especially salts of alkali metals, alkaline earth metals, metals of Groups IIB, IIIA or VIII of the Periodic System of Elements, ammonium salts or salts of organic amines. Examples are, especially, sodium-, potassium-, calcium-, magnesium-, zinc-, aluminium-, ammonium-, trialkylammonium- and tris(hydroxyethyl)ammonium salts.

Preferred compounds of formula II are those wherein n is 1.

Preferred compounds II are further those in which $R^1$, $R^2$, $R^3$ and $R^4$ are H, $C_1$–$C_4$ alkyl, —COOH, —COOZ or $C_1$–$C_4$ alkyl substituted by —COOH or —COOZ. More preferred are compounds in which $R^4$ is —COOH, —COOZ or alkyl substituted by —COOH or —COOZ.

Most preferred are compounds of formula II in which at least one of $R^1$, $R^2$, $R^3$ and $R^4$ is —COOH or alkyl substituted by —COOH and at least one of these substituents is —COOZ or alkyl substituted by —COOZ.

Most especially preferred are compounds of formula II containing one —COOZ group and one —COOH group on adjacent carbon atoms.

Specific examples of compounds of formula I include:
Methyl benzothiazol-2-ylthio acetate
Phenyl benzothiazol-2-ylthio acetate
Ethyl (5-trifluoromethylbenzothiazol-2-ylthio) acetate
n-Propyl (5-carboxybenzothiazol-2-ylthio) acetate
o-Octyl (5-ethoxycarbonylbenzothiazol-2-ylthio) acetate
n-Dodecyl (6-methylsulphonylbenzothiazol-2-ylthio) acetate
Ethyl 3-(benzothiazol-2-ylthio) propionate
Allyl 3-(benzothiazol-2-ylthio) propionate
Cyclohexyl 3-(benzothiazol-2-ylthio) propionate
n-Octadecyl 3-(benzothiazol-2-ylthio) propionate
Methyl 3-(6-aminobenzothiazol-2-ylthio) propionate
Cyclohexyl 3-(6-aminobenzothiazol-2ylthio) propionate
Ethyl 3-(benzothiazol-2-ylthio)-2-methyl propionate
iso-Butyl 4-(benzothiazol-2-ylthio) butyrate
Ethyl 3-(benzothiazol-2-ylthio) butyrate
2-Ethylhexyl 3-(benzothiazol-2-ylthio) butyrate 2-Methoxyethyl 3-(benzothiazol-2-ylthio)-3-methyl butyrate
Diisopropyl benzothiazol-2-ylthio malonate
Dimethyl benzothiazol-2-ylthio succinate
Diethyl benzothiazol-2-ylthio succinate
Diisopropyl benzothiazol-2-ylthio succinate
Di-n-butyl benzothiazol-2-ylthio succinate
Di-i-octyl benzothiazol-2-ylthio succinate
Di-n-decyl benzothiazol-2-ylthio succinate
Di-n-octadecyl benzothiazol-2-ylthio succinate
Di-2-ethylhexyl benzothiazol-2-ylthio succinate
Dicyclohexyl benzothiazol-2-ylthio succinate
Diphenyl benzothiazol-2-ylthio succinate
Dibenzyl benzothiazol-2-ylthio succinate
Di-(4-methylphenyl) benzothiazol-2-ylthio succinate
Butyl methyl benzothiazol-2-ylthio succinate
Methyl phenyl benzothiazol-2-ylthio succinate
Ethyl benzyl benzothiazol-2-ylthio succinate
Methyl hydrogen benzothiazol-2-ylthio succinate
Ethyl hydrogen benzothiazol-2-ylthio succinate
2-Ethylhexyl hydrogen benzothiazol-2-ylthio succinate
Di-n-propyl (5-methylbenzothiazol-2-ylthio) succinate
Di-n-hexyl (6-ethylbenzothiazol-2-ylthio) succinate
Di-but-3-enyl (4-isopropylbenzothiazol-2-ylthio) succinate
Methyl allyl (7-t-butylbenzothiazol-2-ylthio) succinate
Dipentyl (5-n-hexylbenzothiazol-2-ylthio) succinate
Dicyclopentyl (6-[1,1,3,3-tetramethylbutyl]-benzothiazol-2-ylthio succinate
Diphenyl (6-cyclohexylbenzothiazol-2-ylthio) succinate
Di-naphthyl (7-benzylbenzothiazol-2-ylthio) succinate
Dibenzyl (6-methoxybenzothiazol-2-ylthio) succinate
Ethyl methyl (5-methoxybenzothiazol-2-ylthio) succinate
Benzyl phenyl (5-ethoxycarbonylbenzothiazol-2-ylthio) succinate
Methyl hydrogen (4-methylthiobenzothiazol-2-ylthio) succinate Butyl hydrogen (6-methylsulphonylbenzothiazol-2-ylthio) succinate
Di-1,1,3,3-tetramethylbutyl (4-fluorobenzothiazol-2-ylthio) succinate
Dioctadecyl (7-bromobenzothiazol-2-ylthio) succinate
Di-n-nonyl (6-chlorobenzothiazol-2-ylthio) succinate
Dimethyl (4-phenylbenzothiazol-2-ylthio) succinate
Diethyl (6-nitrobenzothiazol-2-ylthio) succinate
Diisopropyl (5-cyanobenzothiazol-2-ylthio) succinate
Di-iso-butyl (5-carboxybenzothiazol-2-ylthio) succinate
Di-n-hexyl (7-hydroxybenzothiazol-2-ylthio) succinate
Di-ethoxyethyl (6-chloro-4-methylbenzothiazol-2-ylthio) succinate
n-Octyl hydrogen (5-chloro-6-n-butylbenzothiazol-2-ylthio) succinate
Benzyl hydrogen (4-bromo-5-n-hexylbenzothiazol-2-ylthio) succinate
Phenyl hydrogen (5-nitro-6-n-propylbenzothiazol-2-ylthio) succinate
Naphthyl hydrogen (5-bromo-6-n-propoxybenzothiazol-2-ylthio) succinate
Allyl hydrogen (6-amino-benzothiazol-2-ylthio) succinate
Cyclohexyl hydrogen (6-methylaminobenzothiazol-2-ylthio) succinate
Methoxyethyl hydrogen (5-dimethylaminobenzothiazol-2-ylthio) succinate
n-Octyl hydrogen (7-phenylaminobenzothiazol-2-ylthio) succinate
n-Decyl hydrogen (6-diphenylamino-benzothiazol-2-ylthio) succinate
n-Octadecyl hydrogen (4-benzylaminobenzothiazol-2-ylthio) succinate
Dimethyl (4-morpholinobenzothiazol-2-ylthio) succinate
Diethyl (5-carbamoylbenzothiazol-2-ylthio) succinate
Di-n-propyl (5-methylcarbamoylbenzothiazol-2-ylthio) succinate
Di-n-butyl (5-diethylcarbamoylbenzothiazol-2ylthio) succinate
Di-1,1,3,3-Tetramethylbutyl (6-phenylcarbamoylbenzothiazol-2-ylthio) succinate
Diphenyl (5,6-dimethyl-benzothiazol-2-ylthio) succinate
Dibenzyl (4,5,6-triethylbenzothiazol-2-ylthio) succinate
Diethyl 3-(4,5,6,7-tetramethylbenzothiazol-2-ylthio) succinate
Didodecyl 3-(benzothiazol-2-ylthio)propane-1,2-dicarboxylate
Diethyl 3(benzothiazol-2-ylthio)-propane-1,2-dicarboxylate
Ethyl hydrogen 3-(benzothiazol-2-ylthio)-propane-1,2-dicarboxylate
Butyl hydrogen 3-(benzothiazol-2-ylthio)-propane-1,2-dicarboxylate
Octadecyl hydrogen 3-(benzothiazol-2-ylthio)-propane-1,2-dicarboxylate
Dimethyl 3-(6-trifluoromethylbenzothiazol-2ylthio)-propane-1,2carboxylate
Di-n-butyl 3-(carbmethoxybenzothiazol-2-ylthio)propane-1,2-dicarboxylate
Di-n-octyl 3-(6-aminobenzothiazol-2-ylthio)-propane,2-dicarboxylate
Dibenzyl 3-(5-ethylaminobenzothiazol-2-ylthio)-propane-1,2-dicarboxylate
Methyl octadecyl 3-(4-dibutylaminobenzothiazol-2-ylthio)-propane-1,2-dicarboxylate
Diphenyl 4-(morpholinobenzothiazol-2-ylthio)-propane-1,2-dicarboxylate
Diethyl 1-(benzothiazol-2-ylthio)-propane-1,3-dicarboxylate
Diisopropyl 2-(benzothiazol-2-ylthio)-propane-1,3-dicarboxylate
Dimethyl 3-(benzothiazol-2-ylthio)-3-phenylpropane-1,2-dicarboxylate
Diethyl 3-(benzothiazol-2-ylthio)-3-(4-carboxyphenyl)-propane-1,2-dicarboxylate
Di-n-butyl 3-(benzothiazol-2-ylthio)-3-(2,4-dicarboxyphenyl)-propane-1,2-dicarboxylate
Di-n-hexyl 3-(benzothiazol-2-ylthio)-3,3-diphenylpropane-1,2-dicarboxylate
Dimethyl 1-(benzothiazol-2-ylthio)-butane-1,2-dicarboxylate
Dibenzyl 1-(benzothiazol-2-ylthio)-2-methylpropane-1,2-dicarboxylate
Di-allyl 2-(benzothiazol-2-ylthio)-butane-2,3-dicarboxylate
Diphenyl 1-(benzothiazol-2-ylthio)-butane-2,4-dicarboxylate
Trimethyl 4-(benzothiazol-2-ylthio)-butane-1,2,3-tricarboxylate
Dimethyl hydrogen 4-(benzothiazol-2-ylthio)-butane-1,2,3-tricarboxylate
Diethyl 1-(benzothiazol-2-ylthio)-pentane-1,5-dicarboxylate
Di-n-hexyl 3-(benzothiazol-2-ylthio)-hexane-1,2-dicarboxylate
Tetraethyl 8-(benzothiazol-2-ylthio)-octane-1,3,5,7-tetracarboxylate
Dimethyl 1-(benzothiazol-2-ylthio)-cyclohexane-1,2-dicarboxylate
Diphenyl 4-(benzothiazol-2-ylthio)-cyclohexane-1,2-dicarboxylate
Tri-n-octyl 1-(benzothiazol-2-ylthio)-propane-1,2,3-tricarboxylate
Di-n-pentyl 1-(benzothiazol-2-ylthio)-3-chloropropane-1,2-dicarboxylate
Di-n-nonyl 1-(benzothiazol-2-ylthio)-3-methoxypropane-1,2-dicarboxylate
Di-n-decyl 1-(benzothiazol-2-ylthio)-3-hydroxypropane-1,2-dicarboxylate
Dimethyl 1-(benzothiazol-2-ylthio)-2-phenyl succinate
Diethyl 1-(benzothiazol-2-ylthio)-2-benzyl succinate
Diethyl 2,3-bis-(benzothiazol-2-ylthio)-butane-1,4-dicarboxylate
Sodium methyl benzothiazol-2-ylthio succinate
Potassium ethyl benzothiazol-2-ylthio succinate
Calcium ethyl benzothiazol-2-ylthio succinate
Zinc isopropyl benzothiazol-2-ylthio succinate
Cobalt n-butyl benzothiazol-2-ylthio succinate
Aluminium 2-ethoxy benzothiazol-2-ylthio succinate
Ammonium n-octyl benzothiazol-2-ylthiosuccinate
Methylammonium methyl benzothiazol-2-ylthio succinate
Triethanolammonium methyl benzothiazol-2-ylthio succinate
Octylammonium phenyl benzothiazol-2-ylthio succinate
Cyclohexylammonium benzyl benzothiazol-2-ylthio succinate
Diethylammonium n-butyl benzothiazol-2-ylthio succinate
Tributylammonium methyl benzothiazol-2-ylthio succinate Sodium ethyl 3-(benzothiazol-2-ylthio)-propane-1,2-dicarboxylate
Potassium-n-propyl 3-(benzothiazol-2-ylthio)-propane-1,2-dicarboxylate
Calcium methyl 3-(benzothiazol-2-ylthio)-propane-1,2-dicarboxylate
Zinc benzyl 3-(benzothiazol-2-ylthio)-propane-1,2-dicarboxylate
Aluminium phenyl 3-(benzothiazol-2-ylthio)-propane-1,2-dicarboxylate
Ammonium allyl 3-(benzothiazol-2-ylthio)-propane-1,2-dicarboxylate
Methyl benzoxazol-2-ylthio acetate
Ethyl (6-aminobenzoxazol-2-ylthio) acetate
Isopropyl 3-(benzoxazol-2-ylthio) propionate
n-Dodecyl 4-(benzoxazol-2-ylthio) butyrate
Diethyl benzoxazol-2-ylthio malonate
Diethyl benzoxazol-2-ylthio succinate
Diisopropyl benzoxazol-2-ylthio succinate
Di-t-butyl benzoxazol-2-ylthio succinate
Di-n-decyl benzoxazol-2-ylthio succinate
Di-n-octadecyl benzoxazol-2-ylthio succinate
Di-2-ethylhexyl benzoxazol-2-ylthio succinate
Dicyclohexyl benzoxazol-2-ylthio succinate
Diphenyl benzoxazol-2-ylthio succinate
Dibenzyl benzoxazol-2-ylthio succinate
Di-(4-methylphenyl) benzoxazol-2-ylthio succinate
Butyl methyl benzoxazol-2-ylthio succinate
Methyl phenyl benzoxazol-2-ylthio succinate
Ethyl benzyl benzoxazol-2-ylthio succinate
Methyl hydrogen benzoxazol-2-ylthio succinate
Ethyl hydrogen benzoxazol-2-ylthio succinate
2-Ethylhexyl hydrogen benzoxazol-2-ylthio succinate
Diethyl 3-(benzoxazol-2-ylthio)-propane-1,2-dicarboxylate
Dimethyl 1-(benzoxazol-2-ylthio)-butane-1,2-dicarboxylate
Triethyl 4-(benzoxazol-2-ylthio)-butane-1,2,3-tricarboxylate
Di-n-propyl 1-(benzoxazol-2-ylthio)-pentane-1,5-dicarboxylate
Di-n-octyl 3-(benzoxazol-2-ylthio)-hexane-1,2-dicarboxylate
Tetramethyl 8-(benzoxazol-2-ylthio)-octane-1,3,5,7-tetracarboxylate
Diethyl 2,3-bis-(benzoxazol-2-ylthio)-butane-1,4-dicarboxylate
Zinc methyl benzoxazol-2-ylthio succinate
Ammonium ethyl benzoxazol-2-ylthio succinate
Methyl benzimidazol-2-ylthio acetate
Ethyl (5(or 6)-carboxybenzimidazol-2-ylthio) acetate
Ethyl (5(or 6)-Ethoxycarbonylbenzimidazol-2-ylthio) acetate
Ethyl (5(or 6)-aminobenzimidazol-2-ylthio) acetate
Phenyl 3-(benzimidazol-2-ylthio) propionate
Allyl 4-(benzimidazol-2-ylthio) butyrate
Benzyl 3-(benzimidazol-2-ylthio) butyrate
Benzimidazol-2-ylthio malonate
Diethyl benzimidazol-2-ylthio succinate
Diisopropyl benzimidazol-2-ylthio succinate
Di-t-butyl benzimidazol-2-ylthio succinate
Di-n-decyl benzimidazol-2-ylthio succinate
Di-n-octadecyl benzimidazol-2-ylthio succinate
Di-2-ethylhexyl benzimidazol-2-ylthio succinate
dicyclohexyl benzimidazol-2-ylthio succinate
Diphenyl benzimidazol-2-ylthio succinate
Dibenzyl benzimidazol-2-ylthio succinate
Di-(4-methylphenyl) benzimidazol-2-ylthio succinate
Butyl methyl benzmidazol-2-ylthio succinate
Methyl phenyl benzimidazol-2-ylthio succinate
Ethyl benzyl benzimidazol-2-ylthio succinate
Methyl hydrogen benzimidazol-2-ylthio succinate
Ethyl hydrogen benzimidazol-2-ylthio succinate
2-Ethylhexyl hydrogen benzimidazol-2-ylthio succinate
Diethyl (6(or 5)-ethylbenzimidazol-2-ylthio) succinate
Dimethyl (7(or 4)-benzylbenzimidazol-2-ylthio) succinate
Di-allyl (5(or 6)-ethoxycarbonylbenzimidazol-2-ylthio) succinate
Dibenzyl (6(or-5)-ethoxybenzimidazol-2-ylthio) succinate
Diphenyl (5(or 6)-chlorobenzmidazol-2-ylthio) succinate
Dimethyl 1-(benzimidazol-2-ylthio)-2-phenyl succinate
Diethyl 1-(benzimidazol-2-ylthio)-2-benzyl succinate
Di-n-butyl (5(or 6)-chloro-4 (or 7)-methylbenzimidazol-2-ylthio) succinate
Diphenyl (5,6-dimethylbenzimidazol-2-ylthio) succinate
Butyl methyl (4,5,6-triethylbenzimidazol-2-ylthio) succinate
Di-n-hexyl (4,5,6,7-tetramethylbenzimidazol-2-ylthio) succinate
Methyl hydrogen (5(or 6)-aminobenzimidazol-2-ylthio) succinate
Di-2-ethylhexyl (1-benzimidazol-2-ylthio)-propane-1,2-dicarboxylate
Dimethyl 3-(benzimidazol-2-ylthio)-propane-1,2-dicarboxylate
Diethyl 1-(benzimidazol-2-ylthio)-butane-1,2-dicarboxylate
Trimethyl 4-(benzimidazol-2-ylthio)-butane-1,2,3-tricarboxylate
Dibenzyl 1-(benzimidazol-2-ylthio)-2-methylpropane-1,2-dicarboxylate
Diisopropyl 2-(benzimidazol-2-ylthio)-butane-2,3-dicarboxylate
Diphenyl 1-(benzimidazol-2-ylthio)-pentane-1,5-dicarboxylate
Dibenzyl 3-(benzimidazol-2-ylthio)-hexane-1,2-dicarboxylate
Tetramethyl 8-(benzimidazol-2-ylthio)-octane-1,3,5,7-tetracarboxylate
Di-n-hexyl 1-(benzimidazol-2-ylthio)-cyclohexane-1,2-dicarboxylate
Triethyl 1-(benzimidazol-2-ylthio)-propane-1,2,3-tricarboxylate
Dimethyl 2,3-bis-(benzimidazol-2-ylthio)-butane-1,4-dicarboxylate
Calcium methyl benzimidazol-2-ylthio succinate
Zinc ethyl benzimidazol-2-ylthio succinate
Ammonium isopropyl benzimidazol-2-ylthio succinate
Tributylammonium n-octyl benzimidazol-2-ylthio succinate
Sodium ethyl 3-(benzimidazol-2-ylthio)-propane-1,2-dicarboxylate
Calcium ixopropyl 3-(benzimidazol-2-ylthio)-propane 1,2-dicarboxylate
Zinc n-hexyl 3-(benzimidazol-2-ylthio)-propane-1,2-dicarboxylate
Dimethyl (benzothiazol-2-ylthio)-ethane-1,2-dicarboxylate
Diethyl (benzimidazol-2-ylthio)-ethene-1,2-dicarboxylate
Diethyl (benzoxazol-2-ylthio)-ethene-1,2-dicarboxylate Diisopropyl 1-(benzothiazol-2-ylthio)-propene-1,2-dicarboxylate
Di-n-butyl 2-(benzothiazol-2-ylthio)-but-1-ene-2,3-dicarboxylate
2,2'-Bis benzothiazol-2-ylthio acetic anhydride
3,3'-Bis benzothiazol-2-ylthio propionic anhydride
2,2'-Bis benzimidazol-2-ylthio acetic anhydride
Benzothiazol-2-ylthio succinic anhydride
5-Methylbenzothiazol-2-ylthio succinic anhydride
6-Aminobenzothiazol-2-ylthio succinic anhydride
5,6-Dimethylbenzothiazol-2-ylthio succinic anhydride
4,5,6-Triethylbenzothiazol-2-ylthio succinic anhydride
4,5,6,7-Tetramethylbenzothiazol-2-ylthio succinic anhydride
Benzoxazol-2-ylthio succinic anhydride
Benzimidazol-2-ylthio succinic anhydride
3-(Benzothiazol-2-ylthio)-propane-1,2-dicarboxylic anhydride
3-(Benzoxazol-2-ylthio)-propane-1,2-dicarboxylic anhydride
3-(Benzimidazol-2-ylthio)-propane-1,2-dicarboxylic anhydride
4-(Benzothiazol-2-ylthio)-3-ethoxycarbonyl-butane-1,2-dicarboxylic anhydride.

Some of the compounds useful as components (B) of the compositions according to the invention are known. For example, compounds having the formula

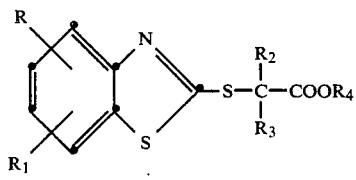

wherein R and $R_1$ are H, alkyl, alkoxy, OH, alkanoyloxy, $NO_2$, $NH_2$, alkanoylamino or halogen and $R_2$, $R_3$ and $R_4$ are H or alkyl are described in Jap. Kokai 79/3064, ref. Chem. Abstr. 90 (1979), 186930q. 6-Alkoxybenzimidazol-2-ylthioglycolic acid esters are described in Indian J. Chem. 3 (1965), 397–401, ref. Chem. Abstr. 64 (1966), 3519e.

Likewise, compounds having the formula

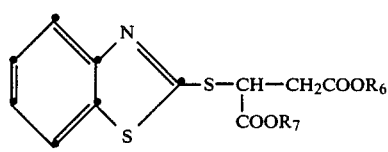

in which $R_6$ and $R_7$ are 3–12 C hydrocarbon radicals or oxahydrocarbon radicals containing from 3–12 carbon and oxygen atoms, are described in U.S. Pat. No. 2,725,364.

Still further, compounds having the formula:

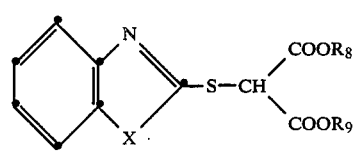

in which X has its previous significance and $R_8$ and $R_9$ are $CH_3$, $C_2H_5$ or $(CH_2)_3CH_3$ are described in Japan Kokai No. 7733532.

Further known compounds are those of formula

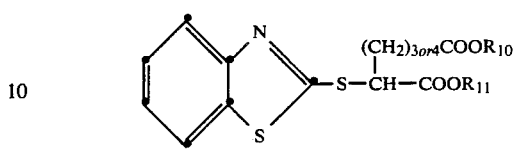

in which $R_{10}$ and $R_{11}$ are methyl or ethyl, which are disclosed in Bull. Chem. Soc. Japan, 52, 267 (1979).

On the other hand, many of the compounds used as components (B) are novel compounds and, as such, form part of the present invention.

One preferred group of novel compounds according to this invention are compounds of formula II

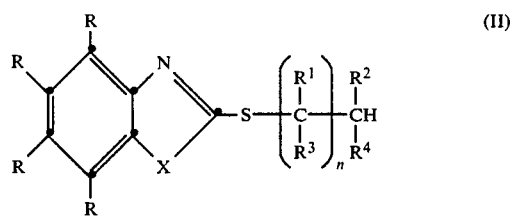

wherein R, $R^1$, $R^2$, $R^3$, $R^4$, n and X have their previous significance provided that, when n is one and $R^1$ or $R^3$ is —COOZ, then $R^2$ or $R^4$ may not be —COOZ or a group —alkyl—COOZ and, when n is zero and $R^2$ is —COOZ, $R^4$ may not be —COOZ, or alkyl —COOZ, further provided that the residue:

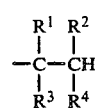

contains two, three or four residues —COOZ or one or two anhydride groups.

Another preferred group of novel compounds are the partial esters viz. compounds having the formula II in which R, n, X, $R^1$, $R^2$, $R^3$ and $R^4$ have their previous significance provided that the residue —[C($R^1$)($R^3$)-]$_n$—CHR$^2$R$^4$ contains one, two or three residues —COOZ and at least one group —COOH.

A third preferred group of novel compounds are the cyclic anhydrides viz. compounds of formula II in which R, n, X, $R^1$, $R^2$, $R^3$ and $R^4$ have their previous significance provided that the residue —[C($R^1$)($R^3$)-]$_n$—CHR$^2$R$^4$ contains one or two groups of formula III or IIIa.

The components (B), whether they be known or novel compounds can be prepared by various processes.

One preferred process is that which is the subject-matter of a separate patent application now U.S. Pat. No. 4,652,653, namely the reaction of compound of formula

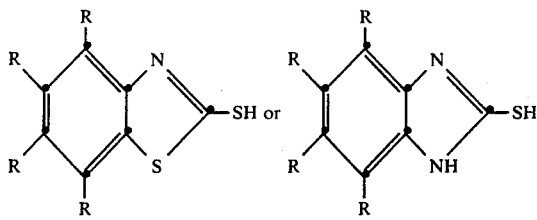

with an unsaturated carboxylic acid ester of formula

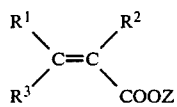

wherein $R^1$, $R^2$ and $R^3$ and Z have their previous significance, in a strongly acid medium.

Another process for producing components (B) is that described in a separate patent Application Ser. No. 610,146 in which, preferably in the presence of a base (a) a compound of formula

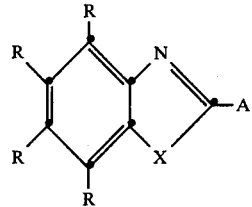

(VI)

in which R and X have their previous significance and A is a leaving group e.g. Cl, Br, I or p-tosyloxy, is reacted with a compound of formula

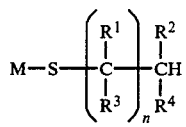

(VII)

in which $R^1$ to $R^4$ and n have their previous significance and M is hydrogen or a cation e.g. an alkali metal-, alkaline earth metal- or ammonium cation; or (b) a compound of formula

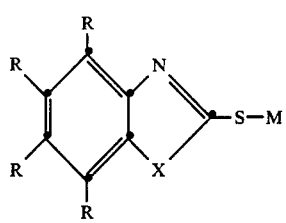

(VIII)

is reacted with a compound of formula

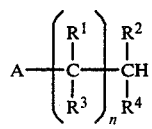

(IX)

and then the product from (a) or (b) is optionally reacted with (c) an alcohol Z—OH wherein Z has its previous significance.

A third method of producing components (B) which are full esters comprises esterifying the corresponding free carboxylic acids with an alcohol Z—OH wherein Z has its previous significance; optionally followed by transesterification using e.g. the methods of Houben-Weyl, "Methoden der Organischen Chemie", Band 8, page 503.

Partial esters may be obtained e.g. by partial hydrolysis of full esters; or by reaction of a cyclic anhydride with one equivalent of an alcohol Z—OH in which Z has its previous significance.

Especially valuable as cyclic anhydrides for use in producing partial ester components (B), are compounds having the formula

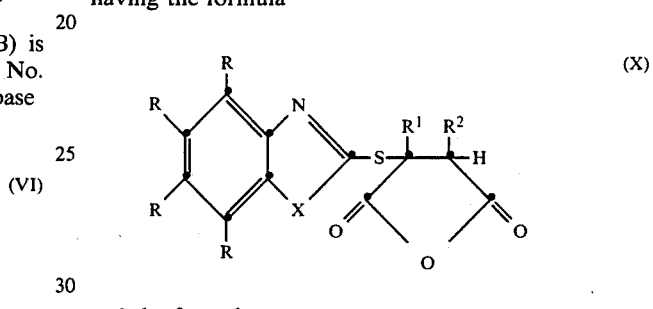

(X)

and the formula

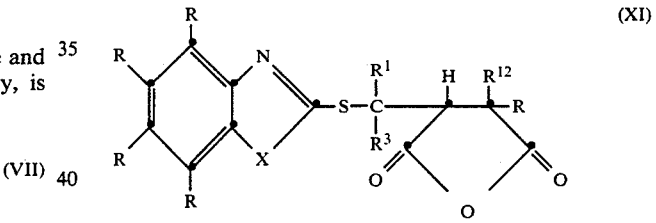

(XI)

in which R, X, $R^1$, $R^2$ and $R^3$ have their previous significance and $R^{12}$ and $R^{13}$ are hydrogen or $C_1$–$C_{10}$ alkyl which may be substituted by one or two groups —COOH or —COOZ and the number of C-atoms in $R^{12}$ and $R^{13}$ together does not exceed 10. Preferably in X and XI the substituents $R^1$, $R^2$, $R^3$, $R^{12}$ and $R^{13}$ are hydrogen.

Anhydrides of aliphatic- or cycloaliphatic monocarboxylic acids of this invention; and cyclic anhydrides of aliphatic- or cycloaliphatic di-, tri- or tetra-carboxylic acids of this invention are new compounds and, as such, form a further aspect of the present invention. Preferred new anhydrides are the cyclic anhydrides of formula X and XI.

The new anhydrides may be prepared by dehydratation of the corresponding carboxylic acids prepared as precursors to the new esters of this invention according to processes described hereinbefore.

Suitable dehydrating agents are acetic anhydride, phosphoryl chloride or carbodiimides such ad dicyclohexylcarbodiimide.

The new anhydrides may also be produced by the addition of a compound of formula

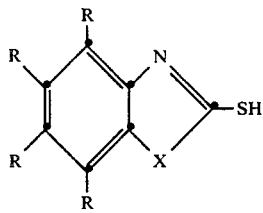

(XII)

wherein R has its previous significance, to a compound of formula XIII or XIV

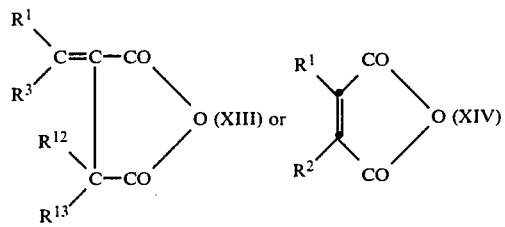

wherein $R^1$, $R^2$, $R^3$, $R^{12}$ and $R^{13}$ have their previous significance.

All the compounds containing a group of formula I are useful as corrosion inhibitors in an application medium selected from:

(a) surface coatings and (b) wholly or partly aqueous media, other than aqueous surface coatings.

With respect to surface coatings (a), the film-forming binder component of the surface coating composition used will depend on whether the surface coating has a non-aqueous base. For non-aqueous surface coatings, the binder may be selected from epoxy resins optionally containing a curing agent, polyurethane resins, aminoplast resins, acrylic resins, polyesters and alkyd resins or their mixtures, Other examples of respective binder systems are polyvinylbutyral, phenolic resins, polyvinyl acetate or its copolymers, polyvinyl chloride or its copolymers, chlorinated rubber or other chlorinated resins, styrene butadiene copolymers, linseed oil and other drying oils and cellulose ester.

For aqueous based surface coatings, there may be used any desired film-formers known for use as binders for aqueous coating compositions e.g. dispersion paints, emulsion paints or electrodepositable paints. The aqueous binder used may be one or more water-soluble or water-dispersible synthetic resins. Examples of such resins are alkyd polyester, acrylic, polyurethane, epoxide, phenoplast and aminoplast precondensate resins and mixtures of these resins, and homo- or copolymers of vinyl ethers, vinyl esters, styrene, vinylidene chloride and vinyl chloride.

The water-borne binder may be optionally crosslinked with aminoplast resins, phenoplast resins, blocked isocyanates, epoxy resins, Mannich bases of phenols or activated carboxylic esters.

There are several methods available for rendering these binders suitable for use in water-borne paints. These methods, which are well known to those skilled in the coatings art, include the incorporation of basic or acidic functional groups which are then neutralised prior to dilution with water.

In addition to the components (A) and (B), the coating composition can also contain further components, for example pigments, dyes extenders and other additives such as are customary for non-aqueous or water-borne coating compositions respectively. The pigments can be organic, inorganic or metalic pigments, for example titanium dioxide, iron oxide, aluminium bronze, phthalocyanine blue etc. It is also possible to use concomitantly anti-corrosion pigments, for example pigments containing phosphates or borates, metal pigments and metal oxide pigments (see Farbe und Lack 88 (1982), 183) or the pigments described in European Patent A No. 54,267. Examples of extenders which can be used concomitantly are talc, chalk, alumina, baryte, mica or silica. Examples of further additives are flow control auxiliaries, dispersing agents, thixotropic agents, adhesion promoters, antioxidants, light stabilisers or curing catalysts.

Particular importance attaches to the addition of basic extenders or pigments. In certain binder systems, for example in acrylic and alkyd resins, these produce a synergistic effect on the inhibition of corrosion. Examples of such basic extenders or pigments are calcium carbonate, magnesium carbonate, zinc oxide, zinc carbonate, zinc phosphate, magnesium oxide, aluminiumoxide, aluminium phosphate or mixtures thereof. Examples of pigments are those based on aminoanthraquinone.

The corrosion inhibitors used according to the invention can also first be applied to such basic extenders or pigments, for example by chemisorption from an aqueous solution, and the preparations thus obtained can be added to the coating composition.

In a further preferred embodiment of the invention the corrosion inhibitors are used together with basic ion exchangers or an ion exchanger of this type is first treated with a solution of the inhibitor, and this preparation is then added to the coating composition. Examples of basic ion exchangers are all typical anion exchangers, such as those available commericially, for example under the names Dowex® 1 or 11 or Amberlite® IRA.

Finally, the corrosion inhibitor can also be applied to a neutral carrier. Suitable carriers are, in particular, pulverulent extenders or pigments. This technique is described in greater detail in German Offenlegungsschrift No. 3,122,907.

In addition to the component (B), the coating composition can also contain other organic, metal-organic or inorganic corrosion inhibitors, for example salts of nitroisophthalic acid, tannin, phosphoric esters, technical amines, substituted benztriazoles or substituted phenols, e.g. p-nonylphenoxyacetic acid such as are described in German Offenlegungsschrift No. 3,146,265.

The coating compositions according to the invention are preferably used as a primer on metallic substrates, in particular on iron, steel, copper and aluminium. Here they can function as so-called conversion coatings, in that chemical reactions take place at the interface between the metal and the coating. The coating compositions may also find application in can coating processes. The application of the coatings can be effected by the customary methods, such as spraying, brushing, rollercoating or dipping. One preferred method is electrodeposition which may be either anodic or cathodic, but is preferably cathodic.

Depending on whether the film-former is a resin which dries physically or can be cured by heat or radiation, the curing of the coatings is carried out at room temperature, by stoving or by irradiation.

The corrosion inhibitors can be added to the coating composition during the preparation of the latter, for example during the distribution of the pigment by grinding or the inhibitors are dissolved beforehand in a solvent and the solution is stirred into the coating composition. The inhibitor is used in an amount of 0.1–20% by weight, preferably 0.5–5% by weight, based on the solids content of the coating composition.

The aqueous applicational media (b) may be wholly aqueous or only partly aqueous.

In practice, when the application medium is a wholly or partly aqueous application medium, the amount of component (B) is conveniently within the range of from 0.1 to 50,000 ppm (or 0.00001 to 5% by weight), preferably from 1 to 500 ppm (or 0.0001 to 0.05% by weight), based on the aqueous system.

The inhibitor component (B) may be used alone or in conjunction with other compounds known to be useful in the treatment of aqueous system.

In the treatment of systems which are completely aqueous, such as cooling water systems, air-conditioning system, steam-generating systems, sea-water evaporator systems, hydrostatic cookers, and closed circuit heating or refrigerant systems, further corrosion inhibitors may be used such as, for example, water soluble zinc salts; phosphates; polyphosphates; phosphonic acids and their salts, for example, acetodiphosphonic acid, nitrolotris methylene phosphonic acid and methylamino dimethylene phosphonocarboxylic acids and their salts, for example, those described in German Offenlegungsschrift No. 2632774, hydroxyphosphonoacetic acid, 2-phosphonobutane-1,2,4-tricarboxylic acid and those disclosed in GB Pat. No. 1572406; nitrates, for example sodium nitrate; nitrites e.g. sodium nitrite; molybdates e.g. sodium molybdate; tungstates; silicates e.g. sodium silicate; benzotriazole, bisbenzotriazole or copper deactivating benzotriazole or tolutriazole derivatives or their Mannich base derivatives; N-acyl sarcosines; N-acylimino diacetic acids; ethanolamines; fatty amines; and polycarbocyclic acids, for example, polymaleic acid and polyacrylic acid, as well as their respective alkali metal salts, copolymers of maleic anhydride, e.g. copolymers of maleic anhydride and sulfonate styrene, copolymers of acrylic acid e.g. copolymers of acrylic acid and hydroxyalkylated acrylic acid, and substituted derivatives of polymaleic and polyacrylic acids and their copolymers.

Moreover, in such completely aqueous systems, the inhibitor used according to the invention may be used in conjunction with dispersing and/or threshold agents e.g. polymerised acrylic or methacrylic acid (or its salts) or acrylamide homo- and copolymers.

Further additives may be precipitating agents such as alkali metal orthophosphates, carbonates; oxygen scavengers such as alkali metal sulphites and hydrazines; sequestering agents such as nitrilotriacetic acid and its salts; antifoaming agents such as silicones e.g. polydimethylsiloxanes, distearylsebacamide, distearyl adipamide and related products derived from ethylene oxide and/or propylene oxide condensations, in addition to fatty alcohols, such as capryl alcohols and their ethylene oxide condensates; and biocides e.g. amines, quaternary ammonium compounds, chlorophenols, sulphur-containing compounds such as sulphones, methylene bis thiocyanates and carbamates, isothiazolones, brominated propionamides, triazines, phosphonium compounds, chlorine and chlorine-release agents and organometallic compounds such as tributyl tin oxide may be used.

If the aqueous applicational medium, component (b), is not completely aqueous e.g. an aqueous machining fluid formulation, it may be e.g. a water dilutable cutting or grinding field.

The aqueous machining fluid formulations treated according to the invention may be e.g. metal working formulations. By "metal working" we mean reaming, broaching, drawing, spinning, cutting, grinding, boring, milling, turning, sawing, non-cutting shaping, rolling or quenching. Examples of water-dilutable cutting or grinding fluids into which the corrosion inhibiting compound may be incorporated include:

(a) Aqueous concentrates of one or more corrosions inhibitors, and optionally one or more anti-wear additives, used at dilutions of 1:50 or 1:100, which are usually employed as grinding fluids;

(b) Polyglycols containing biocides, corrosion inhibitors and anti-wear additives which are used at dilutions of 1:20 to 1:40 for cutting operations and 1:60 to 1:80 for grinding;

(c) Semi-synthetic cutting fluids similar to (b) but containing in addition 10 to 25% oil with sufficient emulsifier to render the water diluted product translucent;

(d) An emulsifiable mineral oil concentrate containing, for example, emulsifiers, corrosion inhibitors, extreme pressure/anti-wear additives, biocides, antifoaming agents, coupling agents etc.; they are generally diluted from 1:10 to 1:50 with water to a white opaque emulsion;

(e) A product similar to (d) containing less oil and more emulsifier which on dilution to the range 1:50 to 1:100 gives a translucent emulsion for cutting or grinding operations.

For those partly-aqueous systems in which the aqueous applicational medium is an aqueous machining fluid formulation the inhibitor component (B) may be used singly, or in admixture with other additives e.g. known further corrosion inhibitors or extreme-pressure additives.

Examples of other corrosion inhibitors which may be used in these aqueous systems, in addition to the inhibitor component (B) used according to the invention, include the following groups:

(a) Organic acids, their esters or ammonium, amine, alkanolamine and metal salts, for example, benzoic acid, p-tert-butyl benzoic acid, disodium sebacate, triethanolamine laurate, iso-nonanoic acid, triethanolamine salt of p-toluene sulphonamido caproic acid, triethanolamine salt of benzene sulphonamide caproic acid, triethanolamine salts of 5-ketocarboxylic acid derivatives as described in European Patent No. 41927, sodium N-lauroyl sarcosinate or nonyl phenoxy acetic acid;

(b) Nitrogen containing materials such as the following types: fatty acid alkanolamides; imidazolines, for example, 1-hydroxyethyl-2-oleylimidazolines; oxazolines; triazoles for example, benzotriazoles; or their Mannich base derivatives; triethanolamines; fatty amines; inorganic salts, for example, sodium nitrate; and the carboxy-triazine compounds described in European Patent Application No. 46139;

(c) Phosphorus containing materials such as the following types: amine phosphates, phosphonic acids or inorganic salts, for example, sodium dihydrogen phosphate or zinc phosphate;

(d) Sulphur containing compounds such as the following types: sodium, calcium or barium petroleum sulphonates, or heterocyclics, for example, sodium mercaptobenzothiazole. Nitrogen containing materials, particularly triethanolamine, are preferred.

The following examples further illustrate the present invention. Parts and percentages shown therein are by weight unless otherwise stated, the temperatures are indicated in °C.

EXAMPLE 1

Diethyl benzothiazol-2-ylthio succinate

A. A solution of 39.4 parts of bromosuccinic acid in 200 parts by volume of 10% aqueous sodium carbonate solution is added over 30 min. to a solution of 41.5 parts of 2-mercapto-benzothiazole in 200 parts by volume of 10% aqueous sodium carbonate solution at 80°. The resulting solution is heated at 80° for 2 hours. The resulting slurry is cooled and extracted with chloroform to remove unreacted 2-mercaptobenzothiazole. The aqueous solution is then acidified with concentrated hydrochloric acid and extracted with ether. The ether layer is evaporated and the solid residue is recristallised from aqueous methanol to give benzo-thiazol-2-ylthio succinic acid, m.p. 175°–178° (with decomposition).

NMR ($\delta$ DMSO-$d_6$); 3.15 (d, 2H); 4.95 (t, 1H); 7.20–8.20 (c, 4H);

B. A solution of 10.0 parts of benzothiazol-2-ylthio succinic acid in 150 parts by volume of absolute ethanol is saturated with dry hydrogen chloride gas and stored at room temperature for about 10 hours. The solvent is evaporated in vacuo and the residual oil is purified by short-path distillation to give diethyl benzothiazol-2-ylthio succinate identical to that prepared by the method of U.S. Pat. No. 2,725,382.

'H NMR ($\delta$ dmso-$d_6$) 1.15 (t, 3H); 1.20 (t, 3H); 3.25 (d, 2H); 4.20 (m, 4H); 5.10 (t, 1H); 7.45 (m, 2H); 8.05 (m, 2H).

EXAMPLE 2

Di-n-butyl benzothiazole-2-ylthio succinate, identical to that prepared by the method of U.S. Pat. No. 2,725,364, was prepared in the manner described in Example 1.

'H NMR ($\delta$ CCl$_4$) 0.95 (t, 6H); 1.55 (m, 8H); 3.15 (d, 2H); 4.15 (m, 4H); 5.00 (t, 1H); 7.30 (m, 2H); 7.80 (m, 2H).

EXAMPLE 3

Benzothiazol-2-ylthio succinic anhydride

A solution of 6.18 parts of dicyclohexylcarbodiimide in 30 parts by volume of dimethoxyethane is added dropwise, over 1.5 hours, to a stirred solution of 8.49 parts of benzothiazol-2-ylthio succinic acid prepared as in Example 1A in dimethoxyethane (70 parts by volume). The reaction is exothermic and the temperature is maintained at 25°–27° with cooling. When the addition is complete, stirring is continued for a further 1.5 hours and the precipitated dicyclohexylurea is removed by filtration. The filtrate is evaporated in vacuo and the residual solid is recrystallised from a mixture of dichloromethane and cyclohexane to give benzothiazol-2-ylthio succinic anhydride m.p. 129°–129° (with decomposition).

Calculated: $C_{11}H_7NO_3S_2$; C 49.81; H 2.67; N 5.28; Found: C 49.76; H 2.53; N 5.40.

EXAMPLE 4

Ethyl hydrogen benzothiazol-2-ylthio succinate

A mixture of 6.5 parts of benzothiazol-2-ylthio succinic anhydride and 75 parts by volume of absolute ethanol is heated at reflux for 10 minutes to give a clear solution. This is allowed to cool and is stirred at room temperature for about 12 hours. The ethanol is removed in vacuo and the residual oil is taken up in chloroform (about 80 parts by volume) and extracted with saturated sodium bicarbonate solution. The aqueous phase is separated, stirred with charcoal, filtered and acidified with concentrated hydrochloric acid. The precipitate oil is extracted into ether, washed with water, dried (MgSO$_4$) and evaporated. The product is further purified by chromatography on silica (eluted with ethyl acetate) to give ethyl hydrogen benzothiazol-2-ylthio succinate as a yellow oil (mixture of two isomers).

Calculated: $C_{13}H_{13}NO_4S_2$; C 50.16; H 4.22; N 4.50; Found: C 50.04; H 4.26; N 4.34.

EXAMPLE 5 2-Ethylhexyl hydrogen benzothiazol-2-ylthio succinate as an oil (mixture of two isomers), is prepared in a manner similar to that of Example 4.

Calculated: $C_{19}H_{24}NO_4S_2$; C 57.70; H 6.38; N 3.54; Found: C 57.81; H 6.27; N 3.35.

EXAMPLE 6

Methyl hydrogen benzthiazol-2-ylthio succinate, as an oil (mixture of two isomers), is prepared in a manner similar to that described in Example 4.

'H NMR ($\delta$ CDCl$_3$) 3.10 (d) and 3.25 (d) (2H); 3.70 (s) and 3.75 (s) (3H); 4.85 (t) and 4.95 (t) (1H); 7.45 (m, 2H); 7.85 (m, 4H); 10.75 (s, 1H) (D$_2$O replaceable).

EXAMPLE 7

Octadecylhydrogenbenzothiazol-2-ylthio succinate as a viscous oil (mixture of two isomers), is prepared in a manner similar to that of Example 4.

Calculated: $C_{29}H_{45}NO_4S_2$; C 65.05; H 8.41; N 2.62; S 11.96%; Found: C 65.45; H 8.80; N 2.53; S 11.83%.

'H NMR ($\delta$ CDCl$_3$/DMSO$^{d6}$) 0.85 (t, 3H); 1.25 (s, 32H); 3.0 (d, 2H); 4.0 (m 2H); 4.8 (m, 1H); 7.2 (m, 2H); 7.65 (m, 2H).

EXAMPLE 8

Butylhydrogenbenzothiazol-2-ylthio succinate as an oil (mixture of two isomers), is prepared in a manner similar to that of Example 4.

'H NMR ($\delta$ CDCl$_3$) 0.85 (t, 3H); 1.45 (m, 4H); 3.15 (d, 2H); 4.15 (m, 2H); 4.85 (t, 1H); 7.18 (m, 2H); 7.60 (m, 2H); 9.195 (s, 1H, D$_2$O replaceable)

EXAMPLE 9

3-(Benzothiazol-2-ylthio)-propane-1,2-dicarboxylic anhydride

A suspension of 20 parts 3-(benzothiazol-2-ylthio)-propane-1,2-dicarboxylic acid and 200 parts acetic anhydride is heated at 55° during 1.5 hours. The resulting yellow solution is cooled, poured onto 1000 parts ice-water, stirred until solid to give 3-(benzothiazol-2-ylthio)propane-1,2-dicarboxylic anhydride m.p. 87°–88°.

'H NMR ($\delta$ CDCl$_3$) 3.05 (d, 2H); 3.65 (m, 3H); 7.15 (m, 2H); 7.6 (m, 2H).

EXAMPLE 10 n-Butyl hydrogen 3-(benzothiazol-2-ylthio)-propane-1,2-dicarboxylate

A mixture of 13.95 parts of 3-(benzothiazol-2-ylthio)-propane-2-dicarboxylic anhydride and 3.7 parts of 1-butanol is heated at 55° C. during 7 hours to give butyl-hydrogen-3-(benzothiazol-2-ylthio)-propane-1,2-dicarboxylate as a brown oil (mixture of two isomers).

'H NMR (δ CDCl$_3$) 0.85 (m, 3H); 1.43 (m4H); 2.8 (d, 2H); 3.35 (m, 1H); 3.6 (m, 2H); 4.04 (m, 2H); 7.2 (m, 2H); 7.62 (m, 2H).

EXAMPLE 11 n-Octadecyl hydrogen 3-(benzothiazol-2-ylthio)-propane-1,2-dicarboxylate

Octadecyl hydrogen 3-(benzothiazol-2-ylthio)-propane-1,2-dicarboxylate as an oil (mixture of two isomers), is prepared in a manner similar to that described in Example 10, but using octadecan-1-ol.

'H NMR (δ CDCl$_3$) 0.85 (t, 3H); 1.25 (s, 32H); 2.9 (d, 2H); 3.42 (m, 1H); 3.71 (m, 2H); 4.1 (m, 2H); 7.15 (m, 2H); 7.8 (m, 2H).

EXAMPLE 12

Di(2-ethylhexyl)benzothiazol-2-ylthio succinate 110 parts of 2-ethylhexanol are saturated with dry hydrogen chloride gas at room temperature. 20 parts of benzothiazol-2-ylthio succinic acid are then added and the mixture heated with stirring to 85°. The resulting solution is stirred for 2.5 hours at 85°. Excess 2-ethylhexanol is removed by heating at 90° under a vacuum of 0.1 mm Hg give di(2-ethylhexyl)benzothiazol-2-ylthio succinate as a yellow liquid.

'H NMR (δ CDCl$_3$) 1.0 (t, 12H); 1.5 (m, 18H); 3.3 (d, 2H); 4.2 (m, 4H); 5.2 (t, 1H); 7.2 (m, 2H); 7.8 (m, 2H).

EXAMPLE 13

Diethyl 3-(benzothiazol-2-ylthio)-propane-1,2-dicarboxylate 150 parts of absolute ethanol are saturated with dry hydrogen chloride gas at room temperature. 50 parts of 3-(benzothiazol-2-ylthio)-propane-1,2-dicarboxylic acid are then added and the mixture heated to reflux. The resulting solution is stirred at reflux for 3 hours. Excess ethanol is removed by heating at 90° under a vacuum of 0.1 mm Hg to give diethyl 3-(benzothiazol-2-ylthio)-propane-1,2-dicarboxylate as a yellow liquid.

'H NMR (δ CDCl$_3$) 1.4 (t, 6H); 3.0 (d, 2H); 3.5 (m, 1H); 3.8 (m, 2H); 4.2 (m, 4H); 7.2 (m, 2H); 7.7 (m, 2H).

EXAMPLE 14

Di-n-dodecyl 3-(benzothiazol-2-ylthio)-propane-1,2-dicarboxylate 125 parts of dodecan-1-ol are saturated with dry hydrogen chloride gas at room temperature. 13.5 parts of 3-(benzothiazol-2-ylthio)-propane-1,2-dicarboxylic acid are then added and the mixture heated to 85°. The resulting solution is stirred for 4 hours at 85°. Excess dodecan-1-ol is removed by heating at 90° under a vacuum of 0.01 mm Hg to give di-dodecyl 3-(benzothiazol-2-ylthio)-propane-1,2-dicarboxylate as a yellow liquid.

'H NMR (δ CDCl$_3$) 1.0 (t, 6H); 1.4 (m, 40H); 3.0 (d, 2H); 3.6 (m, 1H); 3.9 (m, 2H); 4.2 (m, 4H); 7.3 (m, 2H); 7.8 (m, 2H).

EXAMPLE 15

Cyclohexyl 3-(benzothiazol-2-ylthio)propionate 120 parts of cyclohexanol are saturated with dry hydrogen chloride gas at room temperature. 35 parts of benzothiazol-2-ylthiopropionic acid are then added and the mixture heated with stirring to 95°. The resulting clear solution is stirred for 40 minutes at 90°–95°. Excess cyclohexanol is removed by heating at 90° under a vacuum of 0.1 mm Hg to give cyclohexyl 3-(benzothiazol-2-ylthio)propionate as a brown oil.

EXAMPLE 16

Ethyl benzothiazol-2-ylthioacetate 55 parts of 2-mercapto-benzothiazole and 450 parts of dry methanol are mixed and stirred at 45°. A solution of 7.8 parts of sodium in 60 parts of dry methanol is then added over 15 minutes at 45° to give a clear solution. 42 parts of ethyl chloroacetate are then added over 10 minutes at 45°–50°. The mixture is then heated to reflux and stirred at reflux for 5 hours. 300 parts of toluene and 200 parts of water are then added, the toluene layer separated off and washed with water. The toluene solution is evaporated to dryness to give ethyl benzothiazol-2-ylthioacetate as an orange oil which solidifies on standing, m.p. 45°–48°.

EXAMPLE 17

16.8 g of finely powdered 2-mercaptobenzothiazole are suspended in 130 ml 70% sulfuric acid and 11.0 g of ethyl acrylate are added dropwise at 0°–10° in the course of 1 hour, with stirring. After further 1.5 hours at 0°–10° the reaction mixture is poured into ice water and extracted with ethyl acetate. The organic phase is separated and the solvent is evaporated. There remain 18.3 g of liquid ethyl 3-(benzothiazol-2-ylthio)-propionate, $n_D^{20} = 1{,}6120$.

Analysis: ($C_{12}H_{13}NO_2S_2$); calculated: C 53.91; H 4.90; N 5.24; O 11.97; S 23.98%; found: C 53.6; H 4.9; N 5.3; O 12.0; S 24.0%.

EXAMPLE 18

16.8 g of finely powdered 2-mercaptobenzothiazole are suspended in 75 ml 70% sulfuric acid and 12.0 g of ethyl crotonate are added dropwise at 0°–10° in the course of 1 hour. After further 5 hours at 0°–10°, the reaction mixture is poured into ice water and extracted with ethyl acetate. The organic phase is separated and the solvent is evaporated. There remains 26.1 g of a liquid, which is ethyl 3-(benzothiazol-2-ylthio)-butyrate, $n_D^{20} = 1{,}5965$.

Analysis: ($C_{13}H_{15}NO_2S_2$); calculated: C 55.49; H 5.37; N 4.98; O 11.37; S 22.79%; found: C 55.7; H 5.4; N 5.0; O 11.4; S 22.5%.

EXAMPLE 19

16.8 g of finely powdered 2-mercaptobenzothiazole are suspended in 150 ml of 70% sulfuric acid and 16.6 g of itaconic acid dimethyl ester are added dropwise at 0°–10° in the course of half an hour, with stirring. After further 16 hours at 0°–10°, the reaction mixture is poured into ice water and extracted with ethyl acetate. The organic phase is separated, dried and the solvent is evaporated. There yields 15.3 g of a solid residue (47.1% of theory). After recrystallisation from cyclohexane there yields 3-(benzothiazol-2-ylthio)-propane-1,2-dicarboxylic acid dimethyl ester, m.p. 46°–47°.

Analysis: ($C_{14}H_{15}NO_4S_2$); calculated: C 51.68; H 4.65; N 4.31; S 19.71%; found: C 51.8; H 4.7; N 4.2; S 19.5%.

EXAMPLE 20

An alkyd resin paint is prepared using the following formulation:
- 40 parts of Alphthalat ®AM 380 (60% solution in xylene), alkyd resin made by Reichhold Albert Chemie AG,
- 10.0 parts of iron oxide red 225 made by Bayer AG,
- 13.6 parts of talc (micronised),
- 13 parts of micronised calcium carbonate (Millicarb, Pluss-Staufer AG),
- 0.3 parts of 8% cobalt naphthenate solution and
- 22.5 parts of 6:40 xylene/ethylglycol mixture, The corrosion inhibitors indicated in the table which follow are previously dissolved in part of the solvent and are added to the paint. The paint is ground with glass beads for 7 days until a pigment and extender particle size of 15 μm is achieved.

The paint is sprayed onto sand-blasted steel sheets measuring 7×13 cm in a layer thickness of approximately 50 μm after drying. After drying at room temperature for 7 days, the samples are cured for 60 minutes at 60°.

Two cross-shaped cuts 4 cm long are cut into the cured paint surface, until the metal is reached, using a Bonder cross-cut device. An edge protection against (Icosit ®225) is applied to the edges in order to protect them.

The samples are now subjected to a salt spray test as specified in ASTM B 117 for a duration of 600 hours. The conditions of the coating is assessed after every 200 hours of weathering, specifically the degree of bubbling (as specified in DIN 53,209) at the cross-cut and on the painted surface and also the degree of rusting (as specified in DIN 53,210) on the entire surface.

At the end of the test, the coating is removed by treatment with concentrated sodium hydroxide solution, and the corrosion of the metal at the cross-cut (as specified in DIN 53,167) and also over the remainder of the surface is assessed. In every case the assessment is made on the basis of a 6-stage scale. The corrosion protection value CP is given by the sum of the assessment of the coating and the assessment of the metal surface. The higher this value, the more effective is the inhibitor under test.

TABLE

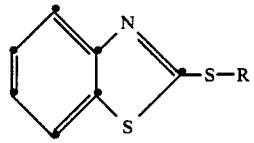

| Example | R | Amount added | Assessment of coating | Assessment of metal | CP |
|---|---|---|---|---|---|
| 1 | —CH(COOC₂H₅)—CH₂—COOC₂H₅ | 2% | 3.3 | 2.7 | 6.0 |
|   |   | 4% | 2.3 | 1.9 | 4.2 |
| 2 | —CH(COOC₄H₉)—CH₂—COOC₄H₉ | 2% | 3.2 | 3.2 | 6.4 |
|   |   | 4% | 3.0 | 3.6 | 6.6 |
| 12 | —CH(COOC₈H₁₇—i)—CH₂—COOC₈H₁₇—i | 2% | 3.6 | 1.7 | 5.3 |
|   |   | 4% | 2.4 | 0.8 | 3.2 |
| 19 | —CH₂—CH(COOCH₃)—CH₂—COOCH₃ | 2% | 3.5 | 2.9 | 6.4 |
|   |   | 4% | 3.7 | 4.3 | 8.0 |
| 13 | —CH₂—CH(COOC₂H₅)—CH₂COOC₂H₅ | 2% | 3.6 | 3.8 | 7.4 |
|   |   | 4% | 3.9 | 3.6 | 7.5 |
| 14 | —CH₂—CH(COOC₁₂H₂₅)—CH₂COOC₁₂H₂₅ | 2% | 3.1 | 1.8 | 4.9 |
|   |   | 4% | 3.3 | 3.2 | 6.5 |
| 15 | —CH₂—CH₂—COO—⟨phenyl⟩ | 2% | 4.6 | 3.2 | 7.8 |
|   |   | 4% | 3.6 | 1.7 | 5.3 |
| 16 | —CH₂—COOC₂H₅ | 2% | 4.3 | 3.7 | 8.0 |
|   |   | 4% | 4.4 | 3.7 | 8.1 |
| 17 | —CH₂—CH₂—COOC₂H₅ | 2% | 1.8 | 0.6 | 2.4 |
|   |   | 4% | 1.7 | 0.6 | 2.3 |
| 18 | —CH(CH₃)—CH₂—COOC₂H₅ | 2% | 3.6 | 3.0 | 6.6 |
|   |   | 4% | 3.2 | 2.7 | 5.9 |

TABLE -continued

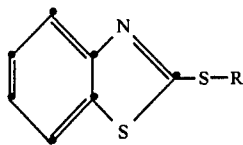

| Example | R | Amount added | Assessment of coating | Assessment of metal | CP |
|---|---|---|---|---|---|
| 3 | ![structure with two C=O groups bridged by O] | 2%<br>4% | 2.8<br>0.6 | 0.6<br>0.6 | 3.4<br>1.2 |
| 9 | —CH$_2$—[structure with two C=O groups bridged by O] | 2%<br>4% | 4.4<br>4.0 | 4.3<br>2.8 | 8.7<br>6.8 |
| 4 | —CH—CH$_2$—COOC$_2$H$_5$<br>\|<br>COOH<br><br>+<br><br>—CH—CH$_2$—COOH<br>\|<br>COOC$_2$H$_5$ | 2%<br>4% | 4.2<br>2.4 | 4.0<br>2.5 | 8.2<br>4.9 |
| 6 | —CH—CH$_2$—COOCH$_3$<br>\|<br>COOH<br><br>+<br><br>—CH—CH$_2$—COOH<br>\|<br>COOCH$_3$ | 2%<br>4% | 4.4<br>2.2 | 1.8<br>0.6 | 6.2<br>2.8 |
| 8 | —CH—CH$_2$—COOC$_4$H$_9$<br>\|<br>COOH<br><br>+<br><br>—CH—CH$_2$—COOH<br>\|<br>COOC$_4$H$_9$ | 2%<br>4% | 4.4<br>4.5 | 4.0<br>3.5 | 8.4<br>8.0 |
| 7 | —CH—CH$_2$—COOC$_{18}$H$_{37}$<br>\|<br>COOH<br><br>+<br><br>—CH—CH$_2$—COOH<br>\|<br>COOC$_{18}$H$_{37}$ | 2%<br>4% | 4.5<br>3.7 | 4.6<br>1.7 | 9.1<br>5.4 |
| 10 | —CH$_2$—CH—CH$_2$—COOC$_4$H$_9$<br>\|<br>COOH<br><br>+<br><br>—CH$_2$—CH—CH$_2$—COOH<br>\|<br>COOC$_4$H$_9$ | 2%<br>4% | 3.5<br>4.4 | 3.3<br>5.0 | 6.8<br>9.4 |
| 11 | —CH$_2$—CH—CH$_2$—COOC$_{18}$H$_{37}$<br>\|<br>COOH<br><br>+ | 2%<br>4% | 4.3<br>4.0 | 3.5<br>3.0 | 7.8<br>7.0 |

TABLE -continued

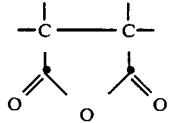

| Example | R | Amount added | Assessment of coating | Assessment of metal | CP |
|---|---|---|---|---|---|
| | —CH$_2$—CH(COOC$_{18}$H$_{37}$)—CH$_2$—COOH | | | | — |
| | Control | — | 1.4 | 1.0 | 2.4 |

What is claimed is:

1. A composition which comprises (A) an aqueous or non-aqueous coating composition suitable for preparing a surface coating which is a paint, and (B) an effective corrosion-inhibiting amount of a compound of formula II

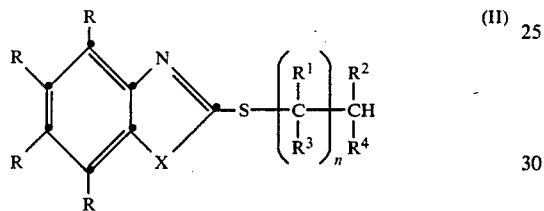

(II)

in which

X is sulphur;

R is each independently of one another hydrogen, alkyl, haloalkyl, alkoxy, alkylthio, alkylsulfonyl, cycloalkyl, phenyl, alkylphenyl, phenylalkyl, halogen, cyano, nitro, hydroxy, —COOH, —COOalkyl or a primary-, secondary- or tertiary-amino or carbamoyl group;

n is 0 or 1;

$R^1$, $R^2$, $R^3$ and $R^4$ are independently hydrogen, alkyl, hydroxyalkyl, haloalkyl, alkoxyalkyl, phenyl, phenylalkyl, said phenyl or said phenylalkyl substituted by one or two of halogen, of alkyl, of alkoxy, of carboxy or of hydroxy; carboxy, alkyl substituted by one, two or three of carboxy or of —COOZ; or —COOZ where Z is $C_1$-$C_{18}$-alkyl, said alkyl interrupted by one or more O or S atoms or by one or more NR$^o$ groups where R$^o$ is $C_1$-$C_{18}$-alkyl, $C_5$-$C_8$-cycloalkyl, phenyl, napthyl, $C_7$-$C_9$-phenylalkyl or $C_7$-$C_{18}$-alkylphenyl; or said alkyl substituted by —SH, by —COOR$^o$, by —CONH$_2$, by —CN or by halogen; $C_2$-$C_1$-hydroxyalkyl or said hydroxyalkyl interrupted by one or more NR$^o$ groups or by one or more oxygen atoms; $C_2$-$C_{18}$-alkenyl, $C_3$—$C_{12}$-cycloalkyl or said cycloalkyl substituted by $C_1$-$C_4$-alkyl, by —OH, by —SH, by —COOR$^o$, by —CONH$_2$, by —CN or by halogen;

$C_7$-$C_9$-phenylalkyl, $C_7$-$C_{18}$-alkylphenyl, or $C_6$-$C_{10}$-aryl or said phenyl or said aryl substituted by $C_1$-$C_{12}$-alkoxy, by $C_1$-$C_{12}$-alkylthio, by —COOH, by —OH, by halogen or by nitro; or (B) is a compound of formula II where the moiety $[-C(R^1)(R^3)]_n$—CH$(R^2)(R^4)$ contains a group of formula III or IIIa

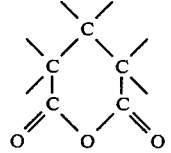

(III)

(IIIa)

or where $R^1$ and $R^2$ or $R^1$ and $R^3$ together form a straight or branched alkylene, or said alkylene substituted by one or two —COOH or by one or two —COOZ; or where $R^1$ and $R^2$ form a direct bond;

with the proviso that at least two of $R^1$, $R^2$, $R^3$ and $R^4$ must contain a carboxy group or a derivative thereof which is a —COOZ group or an anhydride of formula III or IIIa, and that at least one —COOH and one —COOZ, or one anhydride group must be present, and with the further proviso that when n is 1 and $R^1$ or $R^3$ is —COOZ, then neither $R^2$ nor $R^4$ is —COOZ; or when n is 0, $R^2$ or $R^4$ is not —COOZ; or (B) is a non-toxic base addition salt of a compound of formula II which contains a free carboxy group.

2. A composition according to claim 1 where in the compound of formula II $R^1$, $R^2$, $R^3$ and $R^4$ are independently hydrogen, $C_1$-$C_4$-alkyl, —COOH, —COOZ or said alkyl substituted by —COOH or by —COOZ.

3. A composition according to claim 2 where in the compound of formula II $R^4$ is —COOH, —COOZ or $C_1$-$C_4$-alkyl substituted by —COOH or by —COOZ.

4. A composition according to claim 2 where in the compound of formula II at least one of $R^1$, $R^2$, $R^3$ and $R^4$ is —COOH or alkyl substituted by —COOH, and at least one of $R^1$, $R^2$, $R^3$ and $R^4$ is —COOZ or alkyl substituted by —COOZ.

5. A composition according to claim 1 where in the compound of formula II Z is $C_1$-$C_{18}$ alkyl, or said alkyl interrupted by oxygen or said alkyl substituted by —OH, by —SH or by halogen, or Z is allyl, cyclohexyl, benzyl, phenyl, tolyl or naphthyl.

6. Composition according to claim 1, wherein, in the compound of formula II, one of the substituents R is hydrogen, $C_1$–$C_4$ alkyl or $C_1$–$C_4$ alkoxy and the other three groups R are each hydrogen.

7. Composition according to claim 6 wherein all four groups R are each hydrogen.

8. Composition according to claim 1, where in the compound of formula II n is 1.

9. Composition according to claim 1 in which one —COOZ group and one COOH group are present on adjacent carbon atoms.

10. Composition according to claim 1 which contains as component (a) an aqueous or non-aqueous coating composition.

11. Composition according to claim 10 wherein component (a) is a non-aqueous coating composition containing, as film-former, an epoxide resin, polyurethane resin, aminoplast resin, acrylic resin, polyester resin, alkyd resin or a mixture of such resins, polyvinylbutyral, polyvinylacetate, polyvinyl chloride, a phenolic resin, a chlorinated rubber, a styrene-butadiene copolymer, a drying oil or a cellulose ester.

12. Composition according to claim 10 wherein component (a) is an aqueous coating composition containing, as film former, an alkyd, polyester, acrylic, polyurethane, epoxide, phenoplast or aminoplast precondensate resin, or a mixture of these resins, or a homo- or co-polymer of vinyl ethers, vinyl esters, styrene, vinylidene chloride or vinyl chloride.

13. Composition according to claim 12 which also contains a pigment, dyestuff, filler or other customary additive for surface coatings.

14. Composition according to claim 13 which contains a basic filler or basic pigment.

15. Composition according to claim 10 containing, apart from component (B), one or more further corrosion inhibitors which are organic, metallorganic or inorganic compounds.

16. Composition according to claim 10 containing 0.1 t 20 weight % of component (B), based on the solids content of the coating.

17. Composition according to claim 16 containing 0.5 to 5 weight % of component (B), based on the solids content of the coating.

18. Composition according to claim 1 wherein the applicational medium is a wholly or partly aqueous non-coating medium.

19. Composition according to claim 18 containing 0.1 ppm to 5 weight % of component (B), based on the total weight of the applicational medium.

20. Composition according to claim 18 wherein the aqueous system is a cooling water system, an air-conditioning system, a steam-generating system, a seawater evaporator, a hydrostatic cooker, a closed circuit heating or refrigerant system, an aqueous scouring or metal-working formulation, an antifreeze composition or a water-based hydraulic fluid composition.

21. Composition according to claim 18 containing in addition to component (B), one or more other corrosion inhibitors, dispersing agents, precipitation agents, oxygen scavengers, complexing agents, anti-foam agents or biocides.

22. A compound of formula II

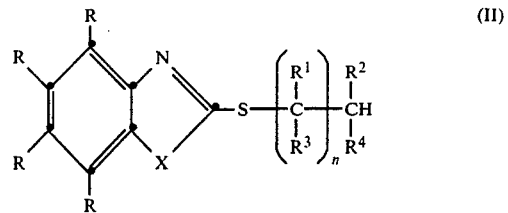

in which
X is sulphur;
R is each independently of one another hydrogen, alkyl, haloalkyl, alkoxy, alkylthio, alkylsulfonyl, cycloalkyl, phenyl, alkylphenyl, phenylalkyl, halogen, cyano, nitro, hydroxy, —COOH, —COOalkyl or a primary-, secondary- or tertiary-amino or carbamoyl group;
n is 0 or 1;
$R^1$, $R^2$, $R^3$ and $R^4$ are independently hydrogen, alkyl, hydroxyalkyl, haloalkyl, alkoxyalkyl, phenyl, phenylalkyl, said phenyl or said phenylalkyl substituted by one or two of halogen, of alkyl, of alkoxy, of carboxy or of hydroxy; carboxy, alkyl substituted by one, two or three of carboxy or —COOZ; or —COOZ where
Z is $C_1$–$C_{18}$-alkyl, said alkyl interrupted by one or more O or S atoms or by one or more NR° groups where R° is $C_1$–$C_{18}$-alkyl, $C_5$–$C_8$-cycloalkyl, phenyl, naphthyl, $C_7$–$C_9$-phenylalkyl or $C_7$–$C_{18}$-alkylphenyl; or said alkyl substituted by —SH, by —COOR°, by —CONH$_2$, by —CN or by halogen; $C_2$–$C_{10}$-hydroxyalkyl or said hydroxyalkyl interrupted by one or more NR° groups or by one or more oxygen atoms; $C_2$–$C_{18}$-alkenyl, $C_3$–$C_{12}$-cycloalkyl or said cycloalkyl substituted by $C_1$–$C_4$-alkyl, by —OH, by —SH, by —COOR°, by —CONH$_2$, by —CN or by halogen; $C_7$–$C_9$-phenylalkyl, $C_7$–$C_{18}$-alkylphenyl, or $C_6$–$C_{10}$-aryl or said phenyl or said aryl substituted by $C_1$–$C_{12}$-alkoxy, by $C_1$–$C_{12}$-alkylthio, by halogen or by nitro; or
is a compound of formula II where the moiety $[-C(R^1)(R^3)]_n-CH(R^2)(R^4)$ contains a group of formula III or IIIa

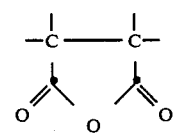

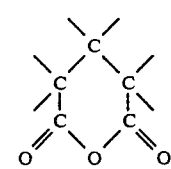

or where $R^1$ and $R^2$ or $R^1$ and $R^3$ together form a straight or branched alkylene, or said alkylene substituted by one or two —COOH or by one or two —COOZ; or where $R^1$ and $R^2$ form a direct bond;

with the proviso that at least two of $R^1$, $R^2$, $R^3$ and $R^4$ must contain a carboxy group or a derivative thereof which is a —COOZ group or an anhydride of formula III or IIIa, and that at least one —COOH and one —COOZ, or one anhydride group must be present, and with the further proviso that when n is 1 and $R^1$ or $R^3$ is —COOZ, then neither $R^2$ nor $R^4$ is —COOZ; or when n is 0, $R^2$ or $R^4$ is not —COOZ.

23. A compound according to claim 22 wherein the moiety

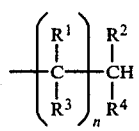

contains one, two or three residues —COOZ and at least one group —COOH.

24. A compound according to claim 22 wherein the moiety

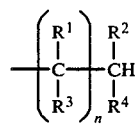

contains one or two groups of formula III or IIIa

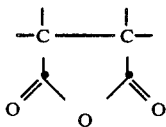

(III)

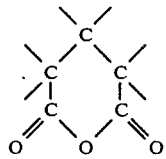

(IIIa)

* * * * *